United States Patent [19]

Hoult

[11] Patent Number: 5,218,428

[45] Date of Patent: Jun. 8, 1993

[54] OPTICAL TRANSMITTANCE APPARATUS FOR FLUIDS

[75] Inventor: Robert A. Hoult, Bethel, Conn.

[73] Assignee: The Perkin-Elmer Corporation, Norwalk, Conn.

[21] Appl. No.: 773,189

[22] Filed: Oct. 8, 1991

[51] Int. Cl.$^5$ ............................................. G01N 21/01
[52] U.S. Cl. .................................. 356/436; 356/246; 356/440; 356/323; 356/235; 250/345
[58] Field of Search ............... 356/246, 440, 428, 436, 356/434, 235, 323; 422/73, 102, 808; 250/575, 345

[56] References Cited

U.S. PATENT DOCUMENTS 3,922,574 11/1975 Whiteley ............................. 310/156

FOREIGN PATENT DOCUMENTS

1020614 11/1977 Canada .
2551190 3/1985 France .
633086 2/1962 Italy .

Primary Examiner—Vincent P. McGraw
Assistant Examiner—LaCharles P. Keesee
Attorney, Agent, or Firm—H. S. Ingham; E. T. Grimes

[57] ABSTRACT

An optical transmittance apparatus has a pair of reference channels of glass rods and a pair of sample channels containing sample fluid. A beam splitter and mirror pass a first portion of an incident beam through an ingoing reference channel, and a second portion through an ingoing sample channel. The first portion is reflected back through an outgoing reference channel, and the second portion back through an outgoing sample channel. The beam splitter and mirror directs the outgoing beams into a common outlet path. A partial disk selectively passes either portion. For positioning the disk, poles of a magnet mounted on the disk axle face windings made about an axis perpendicular to the axle, the windings being on the opposite side of a barrier plate from the poles. Current of one polarity through the windings effects one orientation of the disk, and reversed olarity reorients it perpendicularly.

22 Claims, 4 Drawing Sheets

OPTICAL TRANSMITTANCE APPARATUS FOR FLUIDS

This invention relates to optical transmittance systems and particularly to an optical transmittance apparatus that may be associated with a photometer for determining optical transmittance of a fluid.

BACKGROUND OF THE INVENTION

Photometric measurements of optical transmittance of a liquid involve a probe or other device for passing a light beam through the liquid and passing the beam to a photometric system such as a spectrophotometer. Various configurations have been disclosed for such a device, sometimes called a cuvette. For example U.S. Pat. No. 4,431,307 discloses a cuvette in which radiation is passed through liquid in a container and thence to a photodetector embodied in the cuvette. Coating of side walls minimizes loss of radiation. U.S. Pat. No. 4,648,713 discloses a couvette having at least two regions of different path length through the liquid.

Recent developments in photometric instruments such as spectrophotometers have provided for greater precision, particularly with computerized operation, for example in automated comparisons of sample spectra. An example of a potential application for a new instrument is in-situ detection of near-infrared radiation transmission through gasoline, in which very small variations in transmission are associated with octane levels. A need has evolved for greater precision from the various components of the instruments. One such component is a probe or other apparatus for selectively passing a light beam through a liquid and a reference medium.

It is desirable that optical paths be nearly identical for the optical trains for the sample fluid and the reference medium. Optical transmissions should be very stable and generally immune to significant changes in the refractive index of the liquid, such as from temperature and pressure changes. The overall result should be that a ratio or difference of spectra of the sample and a standard provide a very accurate measure of the spectrum of the fluid.

Further problems exist with analysis of an inflammable fluid such as gasoline. Any electrically driven components in such apparatus, particularly the means for selectively passing the light beams, must be spark-free and preferably free of any electrical current flow. In conventional induction motors, coils generally are disposed radially of and in close proximity to a rotory magnet, and such motors may be isolated from a combustible zone by extending the axle through a seal which is subject to leaks. Coupling may also be effected by coaxial rotary magnets separated by a barrier wall to isolate the combustible zone.

SUMMARY OF THE INVENTION

Therefore, objects of the invention are to provide a novel apparatus for optical transmittance of radiation in fluids, and to provide such an apparatus having improved precision and stability. Other objects are to provide such an apparatus with a dual optical path for the fluid and a reference medium, and to provide such dual apparatus with nearly identical and self-compensating optical trains for the sample fluid and reference medium. A further object is to provide a novel rotational positioning device useful for selectively passing light in such apparatus, with electrical current isolated from vapors.

The foregoing and other objects are achieved by an optical transmittance apparatus for fluids including a housing with a first end section, a second end section spaced from the first end section, and four optical channels extending therebetween. The optical channels consist of a pair of reference channels substantially filled with a reference optical medium, and a pair of sample channels receptive of a sample fluid. The reference channels consist of an ingoing reference channel and an outgoing reference channel, and the sample channels consisting of an ingoing sample channel and an outgoing sample channel.

A beam splitter means is disposed in the first end section to pass a first portion of an incident beam of radiation through the ingoing reference channel, and a second portion of the incident beam through the ingoing sample channel. A reflection means is disposed in the second end section to reflect the passed first portion back through the outgoing reference channel as a reference outgoing beam, and the passed second portion back through the outgoing sample channel as a sample outgoing beam. A recombining means is disposed in the first end section so as to direct the reference outgoing beam and the sample outgoing beam into a common outlet path.

A shutter means such as a rotatable partial disk is advantageously disposed in the housing so as to selectively pass to the recombining means either the reference outgoing beam or the sample outgoing beam such that a selected outgoing beam consists of either or these beams.

In a preferred aspect of the invention, the apparatus further comprises a light source and a transversely adjacent outlet window each disposed in the first end section, the source and the outlet window most preferably being end windows of optical fibers. A collimating lens is disposed between the light source and the beam splitter means to collimate light from the light source to direct the incident beam onto the beam splitter means. A refocusing lens is disposed between the outlet window and the beam splitter means to focus the selected outgoing beam onto the outlet window. Advantageously the beam splitter means and the collating means collectively comprise a single beam splitter and a single diverting mirror.

In a further aspect the reflection means comprises a plane reflecting surface positioned in the second end section perpendicularly to the central axis, and focusing means disposed in the second end section on the central axis to focus the passed first portion and the passed second portion onto the reflecting surface. The arrangement is such that the passed first portion is reflected back through the focusing means and collimated thereby into the outgoing reference channel as the reference outgoing beam, and the passed second portion is reflected back through the focusing means and collimated thereby into the outgoing sample channel as the sample outgoing beam.

A particular arrangement for a positioning means is useful with inflammable fluids. Such a positioning means comprises an axle, a support member, bearing means mounted on the support member for bearing the axle rotationally, magnet means mounted on the axle for positioning a pair of magnetic poles of opposite polarity diametrically spaced with respect to the axle, and one or more windings of electrical conductor affixed to the support member adjacent to the magnetic poles. The windings are made about a winding axis generally perpendicular to the axle, the windings are positioned symmetrically to the axle, and the windings are receptive of reversible direct current so as to interact magnetically with the magnetic means. The passage of current of one polarity through the windings effects a first orientation of the axle, and passage of current of reversed polarity through the windings effects a second orientation of the axle perpendicular to the first orientation.

DETAILED DESCRIPTION OF THE INVENTION

Figure 1:
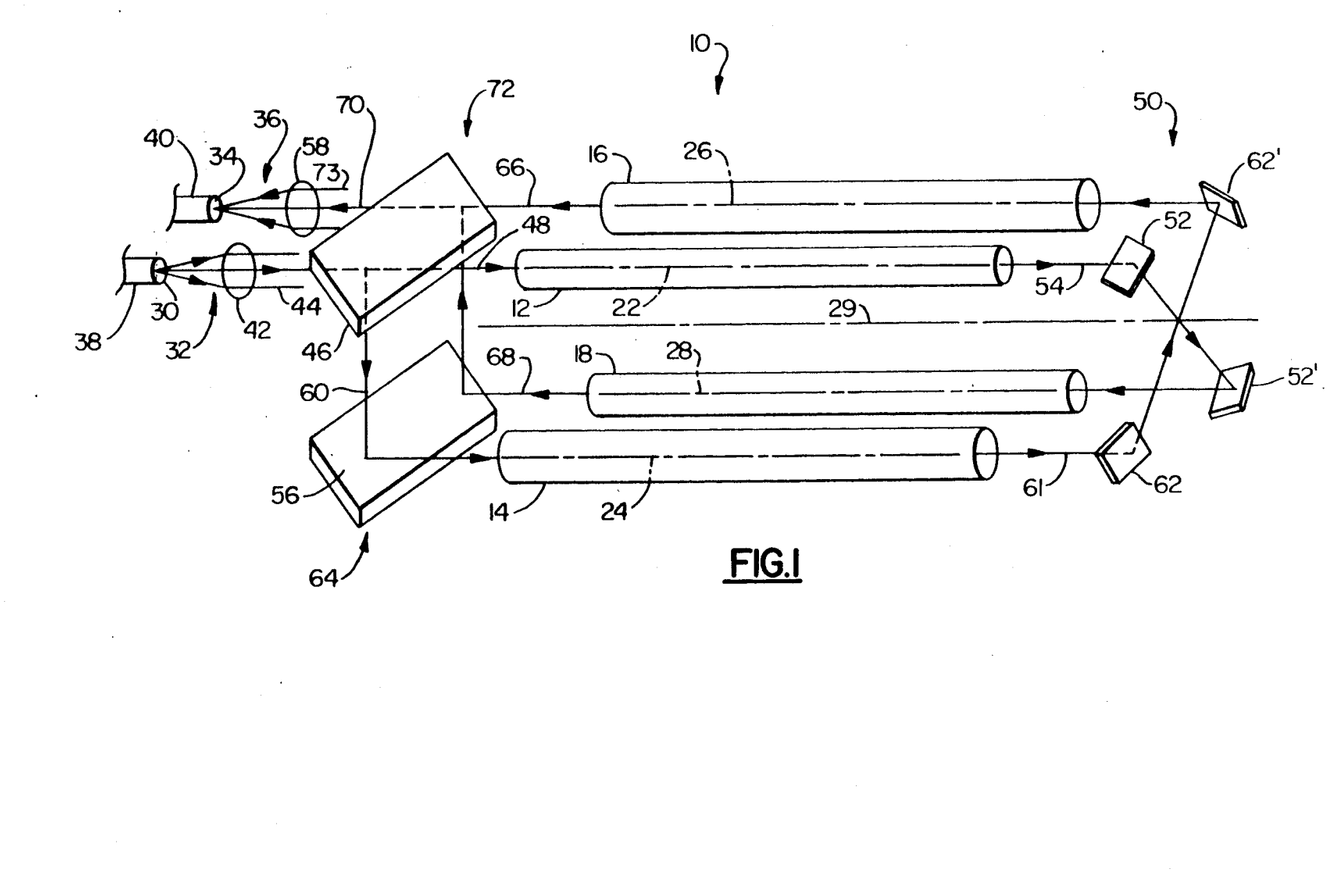
FIG. 1 is a schematic perspective of an apparatus of the invention.

FIG. 1 shows a simple apparatus 10 illustrating the invention. Four optical channels 12,14,16,18 are oriented on respective parallel axes 22,24,26,28 that are spaced radially equally from a central axis 29. A light source 30 directs an ingoing beam of incident light 32 toward the channels, and a transversely adjacent outlet window 34 is receptive of an outgoing beam 36 from the channels. Preferably the source 30 and outlet 34 are respective end windows of an inlet optical fiber 38 and an outlet optical fiber 40. These fibers lead back to a photometric system such as a near-infrared spectrophotometer (not shown) which provides the incident light and analyses the return light.

A collimating lens 42 is disposed to collimate light from the inlet fiber window 30, the window being at the focal point of the lens. A narrow beam 44 is passed to a beam splitter plate 46, nominally a 50% partial mirror, which is disposed to pass a first portion 48 of the incident light beam 32 into one of the channels 12. A reflection means 50, comprising a pair of mirrors 52,52' in this simple case, at the other end of the channels reflects the passed beam back 54 into a second channel 18. A deflecting mirror 56 transversely adjacent the beam splitter 46 deflects the beam 54 back to the partial mirror 46 to be partially reflected into a refocussing lens 58 which focusses the outgoing beam 36 onto the outlet fiber window 34 which is disposed at the focal point of the lens. The beam splitter 46 and the mirror 56 are angled at 45° from each other, to cooperatively direct the beams.

A similar optical train acting in reverse takes the deflected second portion 60 of the split beam from the splitter 46, reflects the passed second portion 61 from the deflecting mirror 56, passes it through a third optical channel 14, reflects it back to a fourth channel 16 via another pair of mirrors 62,62' in the reflection means 50, and straight through the splitter 46 to the refocusing lens 58 and outlet 34.

The four parallel optical channels consist of a pair of reference channels 14,16 substantially filled with a reference optical medium, and a pair of sample channels 12,18 receptive of a sample fluid. Each reference channel may simply contain air (or even vacuum), or preferably a solid rod of glass or polymer or other transparent solid which has an index of refraction closer to that of the sample fluid. One of the reference channels is designated herein and in the claims as an "ingoing reference channel" 14, being the channel that is receptive of and passes through one of the beams 60 from the beam splitter means 64 (such means comprising the splitter 46 and the mirror 56). An "outgoing reference channel" 16 is designated as the channel returning the same beam to the beam splitter means.

Similarly, the sample channels consist of an "ingoing sample channel" 12 receptive of the other incoming beam 48, and an "outgoing sample channel" 18 returning the beam. The sample liquid in these two channels, for example gasoline, is to be tested by its optical absorption of the light beam in the channels. Comparison is to be made with optical absorption through the reference channels.

The four channels are arranged alternately in an array, i.e. the two reference channels are diametrically opposite each other, and the two sample channels are also disposed oppositely.

Also, as shown, the ingoing sample channel 12 receives its beam 48 straight through the splitter 46, while the ingoing reference channel 14 receives a deflected beam 60. It will be appreciated that a reverse arrangement could be utilized. Thus the ingoing reference channel could receive a straight-through beam, and the ingoing sample channel a deflected beam. For this reason it is useful herein and in the claims to define a "direct ingoing channel" as the channel chosen and disposed to be for the straight-through beam, viz. either the ingoing reference channel 14 or the ingoing sample channel 12, and an "indirect ingoing channel" as the other of these channels 12,14 receiving the deflected beam. Such choice will then correspondingly specify a "direct outgoing channel" and an "indirect outgoing channel" correspondingly identified each as the outgoing sample channel 18 or the outgoing reference channel 16. It may be noted that any one choice will automatically designate the others once the beam splitter is set.

Similar definitions apply to the beams. The reflection means 50 reflects a "passed first portion" 61 of the beam from the ingoing reference channel 14 back through the outgoing reference channel 16 as a "reference outgoing beam" 66, and a "passed second portion" 54 of the beam from the ingoing sample channel 12 back through the outgoing sample channel 18 as a "sample outgoing beam" 68. Either of these outgoing beams 66,68 may alternatively be passed selectively (by means not shown in FIG. 1) as a "selected outgoing beam" 70. Also, in the present embodiment, the beam splitter means 64, comprising the beam splitter 46 and the mirror 56, also serves as a recombining means 72 which directs the reference outgoing beam and/or the sample outgoing beam into a common outlet path 73. The beam splitter means and the recombining means could be formed separately, but preferably share the combined components 46,56 for simplicity and equalization of optical paths as explained below.

The reflection means is depicted above as two pairs of plane mirrors. Alternatively this may be a concave mirror (spherical or preferably parabolic) with conjugate foci at the near channel ends, or preferably a lens-mirror combination such as described below.

Figure 2:
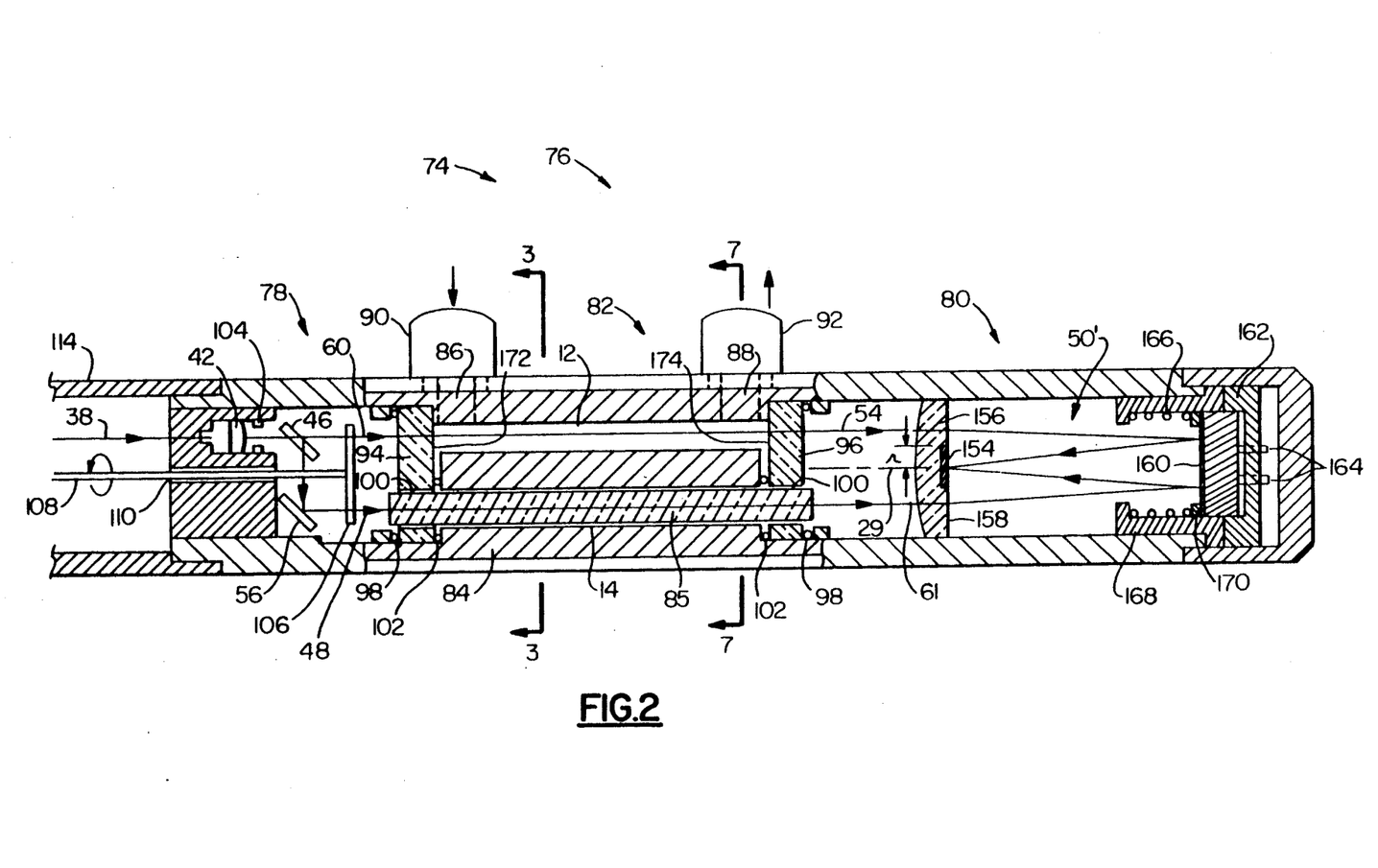
FIG. 2 is a longitudinal section of an apparatus of the invention.
Figures 3, 4, 5A, 7:
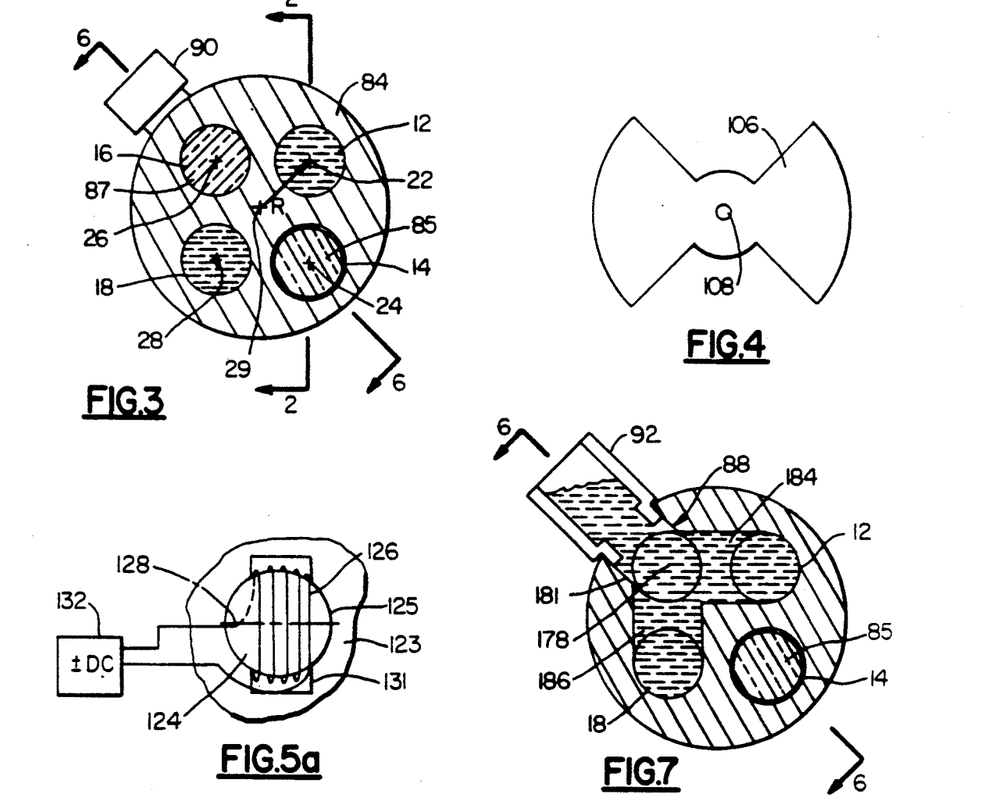
FIG. 3 is a cross section taken at 3—3 of FIG. 2, showing where the longitudinal section 2—2 is taken for the central portion of FIG. 2.
FIG. 4 is an end view of a rotatable disk component of FIG. 2.
FIG. 5a is an end view of a windings component, taken at 5a—5a of FIG. 5.
FIG. 7 is a cross section taken at 7—7 of FIG. 6, further showing where the longitudinal section 6—6 is taken for FIG. 6.

FIGS. 2 and 3 shows an apparatus 74 illustrating some further embodiments and more details. A housing 76 containing various optical components comprises a first end section 78, a second end section 80 spaced from first end section, and a central section 82 therebetween. The central section comprises a substantially solid body 84 made of a material such as aluminum with the four optical channels formed as longitudinal bores therethrough as indicated more in the cross section FIG. 3. Two of the bores 14,16 contain glass (or polymer) rods 85,87. The other two channels 12,18 are receptive of the sample fluid which may be passed longitudinally through each bore by way of an inlet port 86 and an outlet port 88 and associated fluid connectors 90,92. FIG. 2 shows one sample channel 12 and one reference channel 14. The respective axes 22,24,26,28 are uniformly spaced accurately about the central axis.

A transparent solid window 94,96 of glass, polymer or the like, preferably the same as the rods, is mounted in each end section 78,80 adjacent the channels of the central section 82 with seals such as O-rings 98. The rod 85 shown in FIG. 2 extends through a hole 100 in each window and the reference channel is sealed from the fluid with further O-ring seals 102. The sealing arrangement retains the fluid, which may be at high pressure, from leaking into either of the end sections. Additional O-rings and/or other ring seals (not shown) may be provided for redundancy to further ensure against leakage of high pressure fluid.

The retention means also advantageously provides for gas passage between the first end section and the second end section alongside the rod 85 in at least one of the reference channels, so as to equalize gas pressure between the first end section and the second end section. Equalization may be desirable because, in the event of accidental leakage of fluid, it or its vapor can be detected in the more accessible first end section or an extension therefrom.

In FIG. 2 are shown in the first end section 78 the affixed end of optical fiber 38, a collimating lens 42, an aperture 104, the beamsplitter 46 and the deflecting mirror 56. The other fiber 40 and lens 58 (FIG. 1) and similar aperture are not shown, being alongside. A shutter disk 106 is positioned in the housing so as to selectively pass only the first portion 48 (FIG. 1) or the second portion 60 of the light beam through the optical channels, such that a selected outgoing beam 70 consists of the reference outgoing beam or the sample outgoing beam. Although located in the first (left) end section of the housing in the present example, the shutter alternatively may be located in the second (right) end section, preferably between the channels and the reflection means. The shutter conveniently is a partial disk mounted axially in the housing so as to be rotatable to selectively pass the first portion or the second portion. A rotating means such as a manual lever or a stepper motor is connected to the disk by an axle 108 through a bearing 110 to selectively position the disk rotationally. The shutter 106 advantageously has a symmetrical butterfly configuration as shown in FIG. 4.

Figure 5:
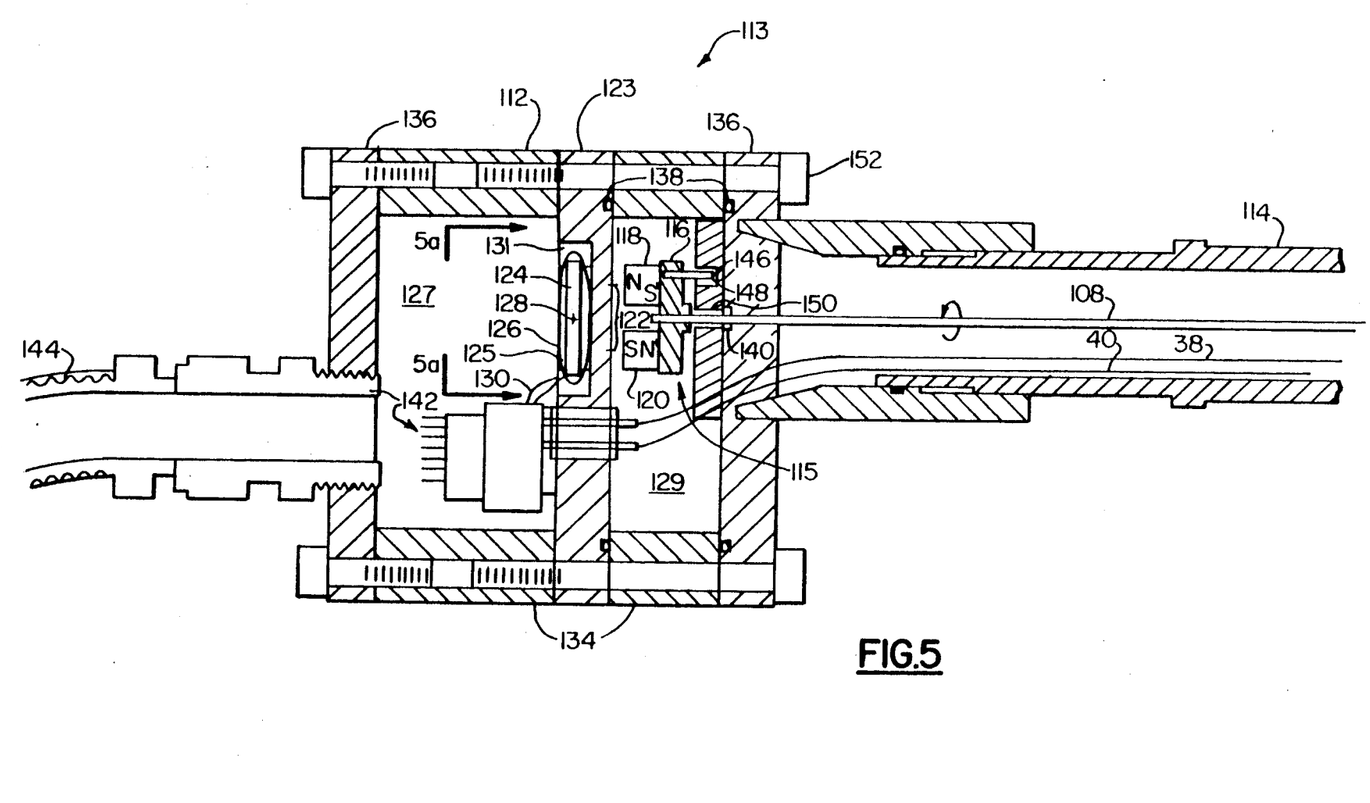
FIG. 5 is a longitudinal section of an embodiment for actuating the disk component of FIG. 4.

In the case of the apparatus being used for testing gasoline or the like as the sample fluid, the motor should be non-sparking. A very suitable rotatable positioning device 113 is illustrated in FIG. 5. The device is mounted in a support structure 112 on an extension 114 from the first end section 78 (FIG. 2). The axle 108 has a magnet means 115 such as a "U" magnet axially attached to the end thereof. In the present aspect the magnet means comprises a flange 116 of magnetic material and two short bar magnets 118,120 mounted thereon in diametrically opposite positions displaced radially from the axle. The magnetic axes 122 of the magnets are parallel to the axle, and the polarities are opposite each other for placing a pair of magnetic poles N,S of opposite polarity diametrically spaced with respect to the axle. (The opposite poles of the magnets are shown as N', S'.)

A support plate advantageously in the form of a disk 124 or the like, preferably of non-permanent magnetic material such as soft iron, is affixed in the structure axially so as to be adjacent to the magnetic poles but on the opposite side of a non-magnetic barrier plate 123 disposed adjacent to the poles perpendicularly to the axle. The disk is conveniently fitted into a shallow hole 125 in the plate and held in place with screws (not shown). The plate isolates a chamber 127 containing electical components, including a coil 126 on the disk, from combustible vapors from the test fluid that may seep into a zone 127 off of the extension 114.

The disk has one or more windings, e.g. about 500 windings of the electrically conducting wire coil 126 wound thereon, the windings being wrapped about a winding axis 128 coinciding with a diameter of the disk perpendicular to the axle as indicated in FIG. 5a. The windings are accommodated in a slot 131 extending across the hole 125. Leads 130 from the coil are connected to a source 132 of direct current (DC) of selectable polarity. Current in one direction through the windows will provide one orientation of the shutter initially positioned to block radiation through one pair of channels. Reversal of the current rotates the device and thereby the shutter to open that pair and block the other pair. A pin 146 in the flange 116 extends into a limited arcuate slot 148 in a bearing plate 150 to delimit rotational positioning of the motor to two perpendicular positions. The present confirmation thus provides for a single switching motor with a vapor barrier (plate 123) between the motor coil 126 and the motor magnet 115.

The end housing 112 is formed conveniently with a pair of cylindrical members 134 positioned between the barrier plate 123 and two end plates 136 to hold the motor components including a bearing 140 for the axle 108. O-rings 138 may be included for seals. This assembly is held together with longitudinal bolts 152. Appropriate connectors 142 and a flexible conduit 144 are utilized. The housing 112 also provides a convenient access for the electrical leads 130 for the motor as well as for the optical fibers 38,40.

In a preferred aspect (FIG. 2) a reflection means 50' comprises a plane reflecting surface 154 positioned perpendicularly to the central axis 29 in the second end section 80, and focusing means disposed in this end section symmetrically on the central axis to focus the passed first portion 54 and the passed second portion 61 onto the reflecting surface 154. More preferably, the focusing means comprises a lens 156 with a planar surface 158 facing away from the optical channels, and a plane mirror 160 facing the planar surface and spaced therefrom. The lens and mirror cooperatively focus the passed first and second portions of the light beam back onto the reflective surface 154 which is a small spot on the planar surface. The small size r of the reflecting spot 154 serves as a further aperture for the beams. The lens-mirror combination may be replaced with a concave lens focused on the spot which, in such case, is a small independent mirror (there being no planar lens surface).

The reflecting spot 154 is centralized on the central axis 29 and has a radius r substantially smaller than the radial spacing R of the channel axes 22,24,26,28 from the central axis (FIG. 3), so as to be substantially outside of the paths of the rays to and from the adjacent optical channels. Thus the passed first and second portions of radiation are each reflected by the reflective spot back to the lens via the plane mirror. This reflection means, being folded, is space efficient. The lens 156 collimates the passed first portion into the outgoing reference channel (not visible in FIG. 2) as the reference outgoing beam in a path similar to but reversed from the ingoing paths 54,61 shown in FIG. 2. Similarly, the passed second portion is collimated into the outgoing sample channel (also not in FIG. 2) as the sample outgoing beam. Thus the reflecting means 50' performs the same basic function as the system of mirrors 50 shown in FIG. 1, but is more efficient optically.

Fine adjustments of the mirror 160 may be provided in its mounting 162. The mirror is held against three adjusting screws 164 (two shown) by a spring 166 that is set in a retaining ring 168 and urged against a seating ring 170 on the mirror. The mirror should be positioned so that the reflective spot 154 is essentially at the reflected focal length of the lens 156.

The aperture 104 should be located approximately at the focal length of the lens 42; similar positioning should be provided for the corresponding aperture for lens 58. It is advantageous for the size of the apertures to be selected so that their images at the spot 154 are slightly (e.g. 10%) larger or smaller than the size of the spot. The purpose is to accommodate small physical distortions in the apparatus, so as to minimize changes in the amount of light passing through.

Figure 6:
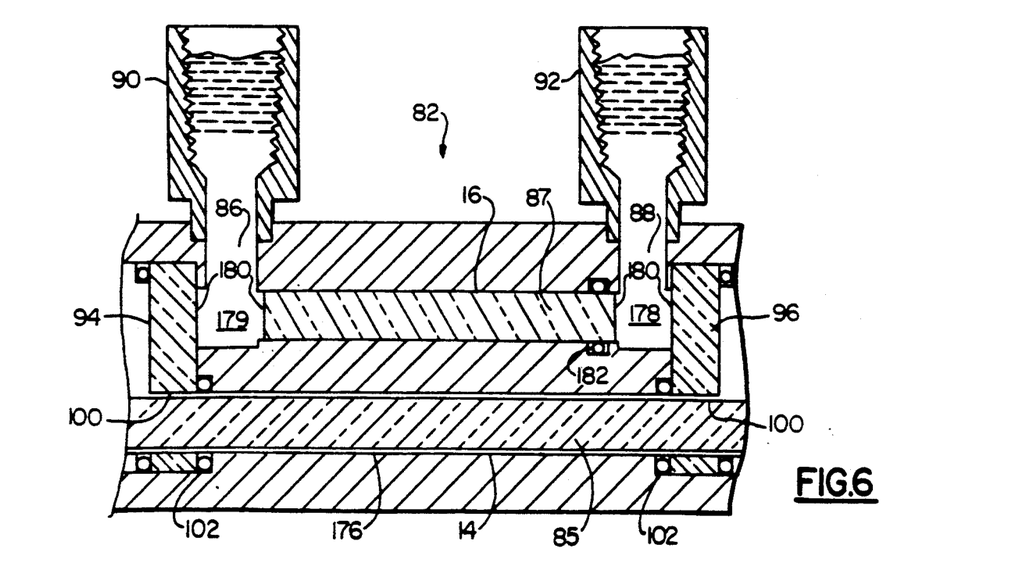
FIG. 6 is a longitudinal section of a central portion of the apparatus of FIG. 2 taken at 6—6 of FIG. 3.

An advantageous arrangement for the central section 82 and windows 94,96 is illustrated in FIG. 6, which is a longitudinal section taken at 6—6 in FIG. 3 and shows the reference channels 14,16 and their glass rods 85,87. In the optical train of the sample channels there are four solid-liquid interfaces between the windows and the liquid, two interfaces 172,174 being visible for the sample channel shown in FIG. 2. In order to compensate for any surface effects, such as deposits from the liquid onto the windows, it is desirable to provide similar interfaces in the optical train of the reference channels.

The rod 85 in a first reference channel (lower rod in FIG. 6) extends through a hole 100 (or slot) in each window and has O-ring seals 102 on the windows but leaves a space 176 along the rod to equalize pressure between ends 78,80 (FIG. 2), as mentioned hereinabove. There are no solid-liquid interfaces for this channel.

The rod 87 of a second (upper) reference channel 16 is shortened and spaced from the adjacent windows 94,96 to provide a shallow space 178,179 for sample fluid in the channel at each end of the shortened rod. The desired four further solid-fluid interfaces 180 are effected in said second reference channel. This shorter rod may be held in place with an O-ring 182 or the like, but there is no need for sealing.

The shallow spaces may be derived from the inlet port 86 and outlet port 88 for the sample fluid, as indicated in FIG. 7 for the outlet port. Each port has a fluid duct with a common leg 181 forming the shallow space 178 and communicating with its associated connector 92, and a Y-branch with two branch legs 184,186 each going to a respective sample fluid channel 12,18. The common legs 178,179 may be oriented on the same side of the housing as shown in FIG. 6. Alternatively (not shown) one port may be oriented 180° from the other, i.e. diametrically opposite, so that the apparatus may be used as a probe inserted into a flowing stream of fluid, with the stream pressure driving fluid through the sample channels.

The foregoing apparatus provides optical paths that are nearly identical except for optical differences between the sample fluid and the reference medium. These paths include duplicate interfaces that comprise the above-described solid-fluid interfaces as well as those associated with the beamsplitter and other optical components. Moreover, except for interfaces, each return (outgoing) beam has substantially the same optical path as its associated ingoing beam. For the fiber optics, the image of the input numerical aperture falls on the output numerical aperture (and vice versa), thereby ensuring good input-output matching. Also, the fiber ends are co-imaged on each other. The transmission will be very stable and generally immune to significant changes in the refractive index of the liquid, such as from temperature and pressure changes. The overall result of these advantages is that a ratio or difference of the sample and spectra will provide a very accurate measure of the spectrum of the fluid.

While the invention has been described above in detail with reference to specific embodiments, various changes and modifications which fall within the spirit of the invention and scope of the appended claims will become apparent only intended to be limited by the appended claims or their equivalents.

I claim:

1. An optical transmittance apparatus for fluids, comprising:

a housing with a first end section, a second end section spaced from the first end section, and four optical channels extending therebetween, the optical channels consisting of a pair of reference channels substantially filled with a reference optical medium and a pair of sample channels receptive of a sample fluid, the reference channels consisting of an ingoing reference channel and an outgoing reference channel, and the sample channels consisting of an ingoing sample channel and an outgoing sample channel;

beam splitter means disposed in the first end section to pass a first portion of an incident beam of radiation through the ingoing reference channel, and a second portion of the incident beam through the ingoing sample channel;

reflection means disposed in the second end section to reflect the passed first portion back through the outgoing reference channel as a reference outgoing beam, and the passed second portion back through the outgoing sample channel as a sample outgoing beam; and recombining means disposed in the first end section so as to direct the reference outgoing beam and the sample outgoing beam into a common outlet path.

2. The apparatus of claim 1 wherein the housing has a central section formed substantially of a solid body with the channels extending therethrough, and the apparatus further comprises retention means for retaining the central portion in sealed relationship with each end section so as to block leakage of sample fluid into either end section, the retention means including space for gas passage between the first end section and the second end section via at least one of the reference channels whereby gas pressure is equalized between the first end section and the second end section.

3. The apparatus of claim 1 further comprising shutter means disposed in the housing so as to selectively pass to the collation means either the reference outgoing beam or the sample outgoing beam such that a selected outgoing beam consists of the reference outgoing beam or the sample outgoing beam.

4. The apparatus of claim 3 wherein the optical channels are parallel with respective axes spaced radially equally from a central axis, and the reference channels and the sample channels are disposed alternately.

5. The apparatus of claim 4 wherein the apparatus further comprises a light source and a transversely adjacent outlet window each disposed in the first end section, collimating means disposed between the light source and the beam splitter means to collimate light from the light source to direct the incident beam onto the beam splitter means, and refocusing means disposed between the outlet window and the beam splitter means to focus the selected outgoing beam onto the outlet window.

6. The apparatus of claim 5 further comprising an inlet optical fiber and an outlet optical fiber each affixed into the first section of the housing so that the light source consists of an end window of the first optical fiber, and the outlet window consists of an end window of the second optical fiber.

7. The apparatus of claim 5 wherein:
the ingoing reference channel and the ingoing sample channel are each prechosen so as to be a direct ingoing channel or an indirect ingoing channel, and the outgoing sample channel and the outgoing reference channel are each correspondingly prechosen to be a direct outgoing channel or an indirect outgoing channel;
the beam splitter means and the recombining means collectively comprise a single beam splitter and a single diverting mirror, the beam splitter being positioned between the collimating means and the direct ingoing channel and further between the refocusing means and the direct outgoing channel, the diverting mirror being positioned transversely from the beam splitter and aligned axially with the indirect ingoing channel and the indirect outgoing channel; and
the beam splitter and the diverting mirror are angled cooperatively so as to divert into the indirect ingoing channel a first or second portion of the incident light corresponding to the indirect outgoing channel, and to divert into the refocusing means a passed first or second portion corresponding to the indirect outgoing channel.

8. The apparatus of claim 4 wherein the respective axes are uniformly spaced accurately about the central axis, and the reflection means comprises a plane reflecting surface positioned in the second end section perpendicularly to the central axis, and focusing means disposed in the second end section on the central axis to focus the passed first portion and the passed second portion onto the reflecting surface, such that the passed first portion is reflected back through the focusing means and collimated thereby into the outgoing reference channel as the reference outgoing beam, and the passed second portion is reflected back through the focusing means and collimated thereby into the outgoing sample channel as the sample outgoing beam.

9. The apparatus of claim 8 wherein the focusing means comprises a lens with a planar surface facing away from the optical channels, and a plane mirror facing the planar surface and spaced therefrom cooperatively so as focus the passed first portion and the passed second portion back onto a reflective spot on the planar surface, the reflective spot being centralized on the central axis and having a radius substantially smaller than the radial spacing, and the reflecting surface comprises the reflective spot, whereby the passed first portion and the passed second portion are reflected by the reflective spot back to the lens via the plane mirror.

10. The apparatus of claim 4 wherein each of the reference channels contains a substantially transparent solid rod constituting the reference optical medium.

11. The apparatus of claim 10 further comprising a pair of transparent solid windows each being disposed in an end section of the housing so that the solid windows delimit the sample channels with four solid-fluid interfaces with the sample fluid, and wherein at least one rod extends from an end section without a solid-fluid interface, and at least one rod is shortened to provide a shallow space for sample fluid in a corresponding reference channel between said rod and one of the solid windows, sufficiently to effect four further solid-fluid interfaces in the reference channels, whereby the solid-fluid interfaces are equalized in number between the reference channels and the sample channels.

12. The apparatus of claim 11 wherein the rod of one of the first reference channels extends between the first end section and the second end section without a solid-fluid interface, and the rod of another of the second reference channels is shortened and spaced from the windows to provide a shallow space for sample fluid in said another of the reference channels at each end of the shortened rod, whereby the further solid-fluid interfaces are effected in said another of the second reference channels.

13. The apparatus of claim 12 wherein the housing has a central section formed substantially of a solid body with the channels extending therethrough, and the apparatus further comprises retention means for retaining the central portion in sealed relationship with each end section so as to block leakage of sample fluid into either end section or into the reference channels, the retention means including space for gas passage between the first end section and the second end section via said one of the first reference channel so as to equalize gas pressure between the first end section and the second end section.

14. The apparatus of claim 3 wherein the shutter means comprises a rotatable partial disk mounted in the housing to selectively pass to the collation means either the reference beam or the sample beam, and positioning means connected to the disk to selectively position the disk rotationally.

15. The apparatus of claim 14 wherein the positioning means comprises an axle, a support member, bearing means mounted on the support member for bearing the axle rotationally, magnet means mounted on the axle for positioning a pair of magnetic poles of opposite polarity diametrically spaced with respect to the axle, and one or more windings of electrical conductor affixed to the support member adjacent to the magnetic poles, the windings being made about a winding axis generally perpendicular to the axle, the windings being positioned symmetrically to the axle, and the windings being receptive of reversible direct current so as to interact magnetically with the magnetic means, such that passage of current of one polarity through the windings effects a first orientation of the axle, and passage of current of reversed polarity through the windings effects a second orientation of the axle perpendicular to the first orientation.

16. The device of claim 15 further comprising a support plate affixed to the support member perpendicular to the axle so as to adjacently face the magnetic poles, with the windings being wound on the support plate.

17. The device of claim 16 wherein the support plate is formed of non-permanent magnetic material 18. An optical transmittance apparatus for fluids, comprising:
   a housing with optical channeling therein including reference channeling substantially filled with a reference optical medium and sample channeling receptive of a sample fluid;
   beam splitter means disposed cooperatively with the channeling so to direct a first portion of an incident beam of radiation into reference channeling, and a second portion of the incident beam into the sample channeling, such that the reference channeling passes a reference beam and the sample channeling passes a sample beam;
   collation means disposed cooperatively with the channeling so as to direct the reference outgoing beam and the sample outgoing beam into a common outlet path; and
   shutter means disposed in the housing so as to selectively pass to the collation means either the reference beam or the sample beam such that a selected outgoing beam consists of the reference outgoing beam or the sample outgoing beam.

19. The apparatus of claim 18 wherein the shutter means comprises a rotatable partial disk mounted in the housing to selectively pass to the collation means either the reference beam or the sample beam, and positioning means connected to the disk to selectively position the disk rotationally.

20. The apparatus of claim 19 wherein the positioning means comprises an axle, a support member, bearing means mounted on the support member for bearing the axle rotationally, magnet means mounted on the axle for positioning a pair of magnetic poles of opposite polarity diametrically spaced with respect to the axle, and one or more windings of electrical conductor affixed to the support member adjacent to the magnetic poles, the windings being made about a winding axis generally perpendicular to the axle, the windings being positioned symmetrically to the axle, and the windings being receptive of reversible direct current so as to interact magnetically with the magnetic means, such that passage of current of one polarity through the windings effects a first orientation of the axle, and passage of current of reversed polarity through the windings effects a second orientation of the axle perpendicular to the first orientation.

21. The device of claim 20 further comprising a support plate affixed to the support member perpendicular to the axle so as to adjacently face the magnetic poles, with the windings being wound on the support plate.

22. The device of claim 21 wherein the support plate is formed of non-permanent magnetic material.

* * * * *